(12) United States Patent
Park et al.

(10) Patent No.: US 6,267,987 B1
(45) Date of Patent: Jul. 31, 2001

(54) POSITIVELY CHARGED POLY[ALPHA-(OMEGA-AMINOALKYL) GLYCOLIC ACID] FOR THE DELIVERY OF A BIOACTIVE AGENT VIA TISSUE AND CELLULAR UPTAKE

(75) Inventors: Jong-Sang Park, Seoul; Min-Hyo Seo, Taejeon, both of (KR)

(73) Assignee: Samyang Corporation, Seoul (KR)

( * ) Notice: Subject to any disclaimer, the term of this patent is extended or adjusted under 35 U.S.C. 154(b) by 0 days.

(21) Appl. No.: 09/210,014

(22) Filed: Dec. 11, 1998

Related U.S. Application Data

(60) Provisional application No. 60/069,526, filed on Dec. 12, 1997.

(51) Int. Cl.[7] .............................. A61K 9/14; C08G 63/08; C12N 15/00
(52) U.S. Cl. ...................... 424/486; 424/468; 424/484; 435/320.1; 435/455; 525/450; 428/354
(58) Field of Search .............................. 435/455; 514/44; 536/23.1; 424/424–426, 433, 468, 489, 497, 484, 486; 528/354; 525/450

(56) References Cited

U.S. PATENT DOCUMENTS

| | | | |
|---|---|---|---|
| 5,399,665 | * | 3/1995 | Barrera et al. ..................... 528/354 |
| 5,654,381 | * | 8/1997 | Hrkach et al. ..................... 525/450 |
| 5,874,064 | * | 2/1999 | Edwards et al. ..................... 424/46 |

OTHER PUBLICATIONS

Edward R. Lee, John Marshall, Craig S. Siegel, Canwen Jiang, Nelson S. Yew, Margaret R.. Nichols, Jennifer B. Nietupski, Robin J. Ziegler, Mathiew B. Lane, Kathryn X. Wang, Nick C. Wan, Ronald K. Scheule, David J. Harris, Alan E. Smith and Seng H. Cheng *Detailed Analysis of Structures and Forumulaions of Cationic Lipids for Efficient Gene Transfer to the Lung* pp. 1701–1717, Human Gene Therapy, vol. 7, pp. 1701–1717, 1996.
*Infectivity of Ribonucleic Acid of Poliovirus on HeLa Cell Monolayers*, Alexander et al. Virology, vol. 5 pp. 172 and 173, 1958.

Ernst Wagner, Matt Cotten, Roland Foisner, and Max L. Birnstiel Transferrin–polycation–DNA complexes: The effect of polycations on the structure of the complex and DNA delivery to cells pp. 4255–4259, P. N. A. S., vol. 88, pp. 4255–4259, 1991.

Ruxandra Gref, Yoshiharu Minamitake, Maria Teresa Peracchia, Vladimir Trubetskoy, Vladimir Tochilin, Robert Langer *Biodegradable Long–Circulating Polymeric Nanospheres*, pp. 1600–1603, Science, vol. 263, pp. 1600–1603, 1994.

Bassima Abdallah, Ahmed Hassan, Corinne Benoist, Daniel Goula, Jean Paul Behr and Barbara A. Demeneix *A Powerful Nonviral Vector for In Vivo Gene Transfer into the Adult Mammalian Brain: Polyethylenimine* pp. 1947 to 1954, Human Gene Therapy, vol. 7, pp. 1947 to 1954, 1996.

Alan H. Jobe, Machiko Ikegami, Soonpin Yel, Jeffrey A. Whitsett and Bruce Trapnell, Surfactant Effects on Aerosolized and Instilled Adenoviral–Mediated Gene Transfer pp. 697 to 704, Human Gene Therapy, vol. 7, pp. 697–704, 1996.

A.V. Kabanov and V.A. Kabanov, Bioconjugate Chem., vol. 6, pp. 7–20, 1995. *DNA Complexes with Polycations for the Delivery of Genetic Material into Cells*, pp. 7–20.

D.F. Williams, Journal of Materials Science, vol. 17, pp. 1233–1246, 1982. Review—Biodegradation of Surgical Polymers, pp. 1233–1246.

James M. Wilson, J. Clin. Invest., vol. 96, pp. 2547–2554, 1995. *Perspectives—Gene Therapy for Cystic Fibrosis: Challenges and Future Directions*, pp. 2547 to 2554.

Anderson (Nature, vol. 392, 25–30), 1998.*
Verma et al. (Nature, vol. 389, 18, 239–242), 1997.*

* cited by examiner

Primary Examiner—Dave Trong Nguyen
(74) Attorney, Agent, or Firm—Thorpe North & Western, LLP

(57) ABSTRACT

A biodegradable, positively-charged aminoalkyl polyester polymer for the delivery of bioactive agents, such as DNA, RNA, oligonucleotides, proteins, peptides, and drugs is disclosed. Biologically active moieties, such as drugs, ligands, and the like, can be coupled to the free amino groups of the polymer.

23 Claims, 2 Drawing Sheets

POSITIVELY CHARGED POLY[ALPHA-(OMEGA-AMINOALKYL) GLYCOLIC ACID] FOR THE DELIVERY OF A BIOACTIVE AGENT VIA TISSUE AND CELLULAR UPTAKE

CROSS-REFERENCE TO RELATED APPLICATIONS

This application claims the benefit of U.S. Provisional Application No. 60/069,526, filed Dec. 12, 1997.

BACKGROUND OF THE INVENTION

This invention relates to delivery of a bioactive agent. More particularly, the invention relates to a composition and method of use thereof for delivering bioactive agents, such as DNA, RNA, oligonucleotides, proteins, peptides, and drugs, to an individual in need thereof.

The concept of using polymers for the controlled release of active drugs and other therapeutic compounds for medical applications has emerged and developed extensively in the last two decades.

When polymers are used for delivery of pharmacologically active agents in vivo, it is essential that the polymers themselves be nontoxic and that they degrade into non-toxic degradation products as the polymer is eroded by the body fluids. Many synthetic biodegradable polymers, however, yield oligomers and monomers upon erosion in vivo that adversely interact with the surrounding tissue. D. F. Williams, 17 J. Mater. Sci. 1233 (1982). To minimize the toxicity of the intact polymer carrier and its degradation products, polymers have been designed based on naturally occurring metabolites. Probably the most extensively studied examples of such polymers are the polyesters derived from lactic or glycolic acid and polyamides derived from amino acids.

A number of bioerodable or biodegradable polymers are known and used for controlled release of pharmaceuticals. Such polymers are described in, for example, U.S. Pat. No. 4,291,013; U.S. Pat. No. 4,347,234; U.S. Pat. No. 4,525,495; U.S. Pat. No. 4,570,629; U.S. Pat. No. 4,572,832; U.S. Pat. No. 4,587,268; U.S. Pat. No. 4,638,045; U.S. Pat. No. 4,675,381; U.S. Pat. No. 4,745,160; and U.S. Pat. No. 5,219,980. Of particular interest is U.S. Pat. No. 5,219,980, which describes ester bonds with side chains of amino-methyl or amino-ethyl groups. The products of hydrolysis of such compounds include 4-amino-2-hydroxy butanoic acid and 4-amino-3-hydroxy butanoic acid, which are not precursors for the twenty naturally occurring alpha-amino acids, and are, therefore, not as fully biocompatible as might be desired.

The biodegradable polymers, polylactic acid, polyglycolic acid, and polylactic-glycolic acid copolymer (PLGA), have been investigated extensively for nanoparticle formulation. These polymers are polyesters that, upon implantation in the body, undergo simple hydrolysis. The products of such hydrolysis are biologically compatible and metabolizable moieties (i.e. lactic acid and glycolic acid), which are eventually removed from the body by the citric acid cycle. Polymer biodegradation products are formed at a very slow rate, hence do not affect normal cell function. Drug release from these polymers occurs by two mechanisms. First, diffusion results in the release of the drug molecules from the implant surface. Second, subsequent release occurs by the cleavage of the polymer backbone, defined as bulk erosion. Several implant studies with these polymers have proven safe in drug delivery applications, used in the form of matrices, microspheres, bone implant materials, surgical sutures, and also in contraceptive applications for long-term effects. These polymers are also used as graft materials for artificial organs, and recently as basement membranes in tissue engineering investigations. 2 Nature Med. 824–826 (1996). Thus, these polymers have been time-tested in various applications and proven safe for human use. Most importantly, these polymers are FDA-approved for human use.

Nanoparticles are hypothesized to have enhanced interfacial cellular uptake because of their sub-cellular size, achieving in a true sense a "local pharmacological drug effect." It is also hypothesized that there would be enhanced cellular uptake of drugs in nanoparticles (due to endocytosis) compared to the corresponding free drugs. Several investigators have demonstrated that nanoparticle-entrapped agents have higher cellular uptake by endocytosis and prolonged retention compared to the free drugs. Thus, nanoparticle-entrapped drugs have enhanced and sustained concentrations inside cells and hence enhanced therapeutic drug effects in inhibiting proliferative response. Furthermore, nanoparticle-entrapped drugs are protected from metabolic inactivation before reaching the target site, as often happens with upon the systemic administration of free drugs. Therefore, the effective local nanoparticle dose required for the local pharmacologic drug effect may be several fold lower than with systemic or oral doses.

Nanoparticles have been investigated as drug carrier systems in cancer therapy for tumor localization of therapeutic agents, for intracellular targeting (antiviral or antibacterial agents), for targeting to the reticuloendothelial system (parasitic infections), as an immunological adjuvant (by oral and subcutaneous routes), for ocular delivery for sustained drug action, and for prolonged systemic drug therapy. 263 Science 1600–1603 (1994).

Because the surfaces of both nanoparticles (or microspheres) and cell membranes are negatively charged, cellular uptake is very low. Nanoparticles and microspheres of PLGA are electrostatically repelled by cell membranes, and thus cannot efficiently penetrate cells.

Since the early efforts to identify methods for delivery of nucleic acids in tissue culture cells in the mid 1950's, H. E. Alexander et al., 5 Virology 172–173 (1958), steady progress has been made toward improving delivery of functional DNA, RNA, and antisense oligonucleotides in vitro and in vivo. Delivery and expression of nucleic acids is a topic that continues to capture scientific attention. Methods for delivering functional non-replicating plasmids in vivo are currently in their infancy, while some success has been achieved in vitro. Current transfection techniques including using cationic lipids, E. R. Lee et al., 7 Human Gene Therapy 1701–1717 (1996), cationic polymers, B. A. Demeneix et al., 7 Human Gene Therapy 1947–1954 (1996); A. V. Kabanov et al., 6 Bioconjugate Chem. 7–20 (1995); E. Wagner, 88 Proc. Nat'l Acad. Sci. USA 4255–4259 (1991), viral vectors, A. H. Jobe et al., 7 Human Gene Therapy 697–704 (1996); J. Gauldie, 6 Curr. Opinion Biotech. 590–595 (1995). Each of the above listed methods has specific disadvantages and limitations. Viral vectors have shown a high transfection efficiency compared to the non-viral vectors, but their use in vivo is severely limited due to several drawbacks, such as targeting only dividing cells, random DNA insertion, risk of replication, and possible host immune reaction. J. M. Wilson et al., 96 J. Clin. Invest. 2547–2554 (1995).

Compared to viral vectors, nonviral vectors are easy to make and less likely to produce immune reactions, and there is no replication reaction. Under some conditions transfection efficiencies close to 100% can be obtained in vitro. In general, however, such nonviral vectors have been found to be ineffective for the introduction of genetic material into cells, and exhibit relatively low gene expression in vivo. For example, various cationic amphiphiles have been used for gene transfection. F. D. Ledley, 6 Human Gene Therapy 1129–1144 (1995). Transfection efficiency using cationic lipids, however, is still not as high as with viral vectors, and there have been complaints of cytotoxicity. The biggest disadvantage of cationic lipids is that they are not metabolites of the body and thus are very difficult to remove therefrom.

Several different classes of cationic polymers have been described for enhancing the uptake of DNA into cells and its egress from endosomes. Dendrimers, are polyamidoamine cascade polymers wherein the diameter is determined by the number of synthetic steps. Dendrimer-DNA complexes have been constructed using dendrimers of different size as well as different drug charge ratios (cationic dendrimer to anionic DNA). These complexes exhibit efficient gene delivery into a variety of cell types in vitro. F. D. Ledley, 6 Human Gene Therapy 1129-1144 (1995). Another type of cationic polymers, polyethylenimine (PI) and poly-L-lysine (PLL), similarly have high uniform positive charge density, will complex with DNA and other nucleic acids, and will transfer nucleic acids into a variety of cells in vitro. These polymers are capable of condensing plasmid DNA to form complexes with varying sizes and charges that may interact with the membrane of cells by ionic interaction and enter cells by endocytosis. These cationic polymers, however, are not biodegradable. Therefore, they are toxic due to accumulation in the body. It takes a few years, for example, to completely degrade PLL in the body.

In view of the foregoing, it will be appreciated that providing a carrier that is non-toxic, biodegradable, and efficient for delivery of nucleic acids and other drugs would be a significant advancement in the art.

BRIEF SUMMARY OF THE INVENTION

It is an object of the present invention to provide a carrier for use in delivery of a nucleic acid, drug, or other bioactive agent to an individual in need thereof.

It is also object of the invention to provide a drug carrier that is nontoxic and biodegradable.

It is another object of the invention to provide a carrier for delivery of nucleic acids that provides good transfection efficiency.

These and other objects can be addressed by providing poly[α-(ω-aminoalkyl) glycolic acid] for use in delivery of a bioactive agent. In a preferred embodiment, the invention comprises a biodegradable polyester polymer represented by the formula

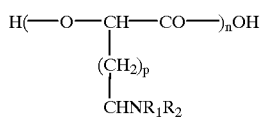

wherein n is the number of repeating monomer units; p is an integer from 2 to 9; and $R_1$ and $R_2$ are selected from the group consisting of H, carbohydrates and derivatives thereof, polyethylene glycol, drugs, and peptides.

In another preferred embodiment, the invention comprises a biodegradable, amphiphilic polyester block copolymer comprising:

(a) a first polymer represented by the formula

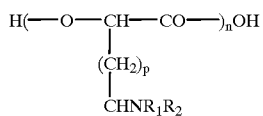

wherein n is the number of repeating monomer units; p is an integer from 2 to 9; and $R_1$ and $R_2$ are selected from the group consisting of H, carbohydrates and derivatives thereof, polyethylene glycol, drugs, and peptides; and (b) a second polymer bonded to the first polymer, wherein the second polymer is a member selected from the group consisting of poly(D-lactic acid), poly(L-lactic acid), poly(DL-lactic acid), poly(D-lactide), poly(L-lactide), poly(DL-lactide), polyglycolic acid, polyglycolides, poly(lactic-co-glycolic acids), and polycaprolactone.

In another preferred embodiment, the invention comprises a biodegradable polyester random copolymer comprising:

(a) a plurality of a first monomer represented by the formula

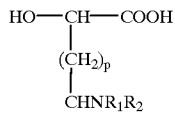

wherein p is an integer from 2 to 9; and $R_1$ and $R_2$ are selected from the group consisting of H, carbohydrates and derivatives thereof, polyethylene glycol, drugs, and peptides; and (b) a plurality of a second monomer selected from the group consisting of D-lactic acid, L-lactic acid, D-lactide, L-lactide, glycolic acid, glycolide, and caprolactone.

In still another preferred embodiment, the invention comprises a pharmaceutical composition comprising a bioactive agent electrostatically coupled to a biodegradable polyester polymer as described above. In yet another preferred embodiment, the invention comprises a pharmaceutical composition comprising a mixture of a drug and a biodegradable polyester polymer as described above.

DETAILED DESCRIPTION

Figure 1:
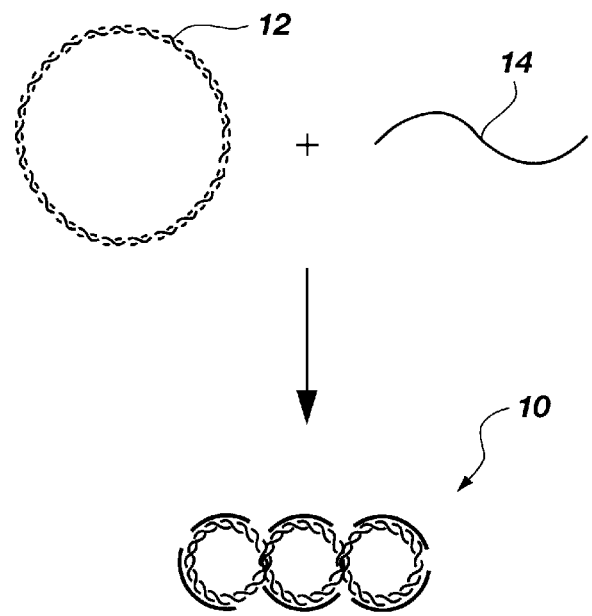
FIG. 1 shows a schematic representation of an illustrative complex of a nucleic acid and poly[α-(ω-aminoalkyl) glycolic acid] according to the present invention.

Before the present composition and method for delivery of a bioactive agent are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a polymer containing "a sugar" includes reference to two or more of such sugars, reference to "a ligand" includes reference to one or more of such ligands, and reference to "a drug" includes reference to two or more of such drugs.

In describing and claiming the present invention, the following terminology will be used in accordance with the definitions set out below.

As used herein, the term "drug" or "bioactive agent" or any other similar term means any chemical or biological material or compound suitable for administration by the methods previously known in the art and/or by the methods taught in the present invention that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anaesthetic effect, or it may be systemic. This invention is not drawn to novel drugs or to new classes of bioactive agents. Rather it is limited to the compositions and methods of delivery of agents that exist in the state of the art or that may later be established as active agents and that are suitable for delivery by the present invention. Such substances include broad classes of compounds normally delivered into the body. In general, this includes but is not limited to: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, both ionized and nonionized drugs may be delivered, as can drugs of either high or low molecular weight. Also included in the scope of these terms are nucleic acids, such as DNA, RNA, and oligonucleotides.

As used herein, "effective amount" means an amount of a drug or bioactive agent that is nontoxic but sufficient to provide the desired local or systemic effect and performance at a reasonable benefit/risk ratio attending any medical treatment.

As used herein, "peptide" means peptides of any length and includes proteins. The terms "polypeptide" and "oligopeptide" are used herein without any particular intended size limitation, unless a particular size is otherwise stated. Typical of peptides that can be utilized are those selected from group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, a "derivative" of a carbohydrate includes, for example, an acid form of a sugar, e.g. glucuronic acid; an amine of a sugar, e.g. galactosamine; a phosphate of a sugar, e.g. mannose-6-phosphate; and the like.

As used herein, "administering" and similar terms mean delivering the composition to the individual being treated such that the composition is capable of being circulated systemically to the parts of the body where the composition binds to targeted cells and is taken up by endocytosis. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

The biodegradable polyester of the present invention, poly[α-(ω-aminoalkyl)glycolic acid], comprises amine groups on the side chains, which are electrostatically attracted to polyanionic compounds such as nucleic acids. Poly[α-(ω-aminoalkyl)glycolic acid] condenses DNA, for example, into compact structures. FIG. 1 shows an illustrative complex 10 formed by the ionic or electrostatic bonding or attraction of plasmid DNA 12 to poly[α-(ω-aminoalkyl) glycolic acid] 14. Upon administration, such complexes of these polycationic polyesters and nucleic acids are internalized into cells through receptor mediated endocytosis. Suitable nucleic acids include DNA, RNA, and specific gene or RNA function inhibitors such as antisense oligonucleotides. The poly[α-(ω-aminoalkyl)glycolic acid] polyesters of the present invention are highly positively charged, which greatly enhances cellular and tissue uptake in the delivery of genes, drugs, and other bioactive agents.

Figure 2:
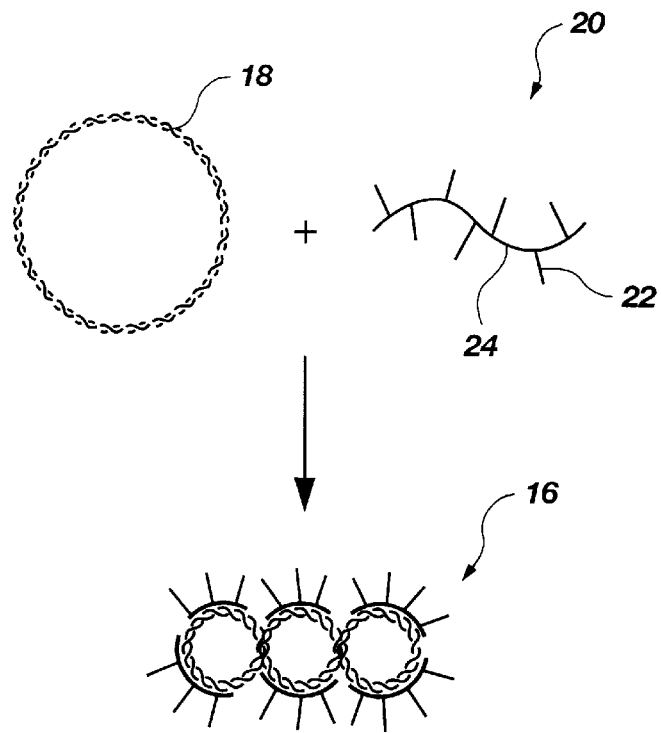
FIG. 2 shows a schematic representation of an illustrative complex of a nucleic acid and a PEG-grafted-poly[α-(ω-aminoalkyl)glycolic acid] polyester.
Figure 3:
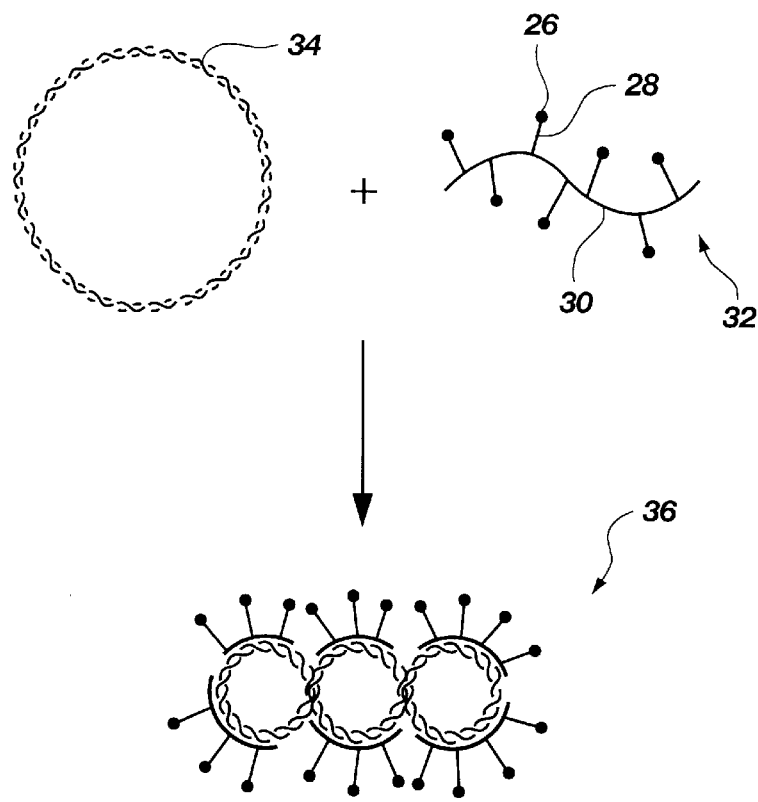
FIG. 3 shows a schematic representation of an illustrative complex of a nucleic acid and a ligand-PEG-grafted-poly[α-(ω-aminoalkyl)glycolic acid] polyester.

The amine groups on the polymer can also be conjugated with molecules such as ligands, inhibitors of immune response, and the like. FIG. 2 shows an illustrative complex 16 formed by The electrostatic attraction of plasmid DNA 18 to a polyethylene glycol-grafted-poly[α-(ω-aminoalkyl) glycolic acid] 20. The polyethylene glycol-grafted-poly[α-(ω-aminoalkyl)glycolic acid] is formed by the conjugation of polyethylene glycol (PEG) 22 to free amine groups on poly[α-(ω-aminoalkyl)glycolic acid] 24. PEG is an FDA-approved polymer known to inhibit the immunogenicity of molecules to which it is attached. The amine groups on the polymer can also be conjugated to ligands for targeting selected cells and/or tissues. The ligands can be attached directly to the amine groups or can be attached via spacer molecules. FIG. 3 illustrates a configuration where a ligand 26 is coupled to a spacer molecule 28 such as a PEG chain, which is in turn coupled to poly[α-(ω-aminoalkyl)glycolic acid] 30. Preferably, only a portion of available amine groups are coupled to the ligand or spacer/ligand such that the net charge of the ligand-spacer-poly[α-(ω-aminoalkyl) glycolic acid] 32 is positive. This positive charge allows the ligand-spacer-poly[α-(ω-aminoalkyl)glycolic acid] 32 to bind electrostatically to plasmid DNA 34, resulting in the formation of a complex 36.

As summarized above, a portion of the amino groups of the poly[α-(ω-aminoalkyl)glycolic acid] can be conjugated to tissue-targeting ligands, which direct the polymer-nucleic acid complex to bind to specific target cells and to penetrate into such cells. In a preferred embodiment, the ligands can be sugar moieties coupled to the amino groups. Such sugar moieties are preferably mono- or oligo-saccharides, such as galactose, glucose, fucose, fructose, lactose, sucrose, mannose, cellobiose, nytrose, triose, dextrose, trehalose, maltose, galactosamine, glucosamine, galacturonic acid, glucuronic acid, and gluconic acid.

The conjugation of an acid derivative of a sugar with the polycation is most preferable. In a preferred embodiment of the present invention, lactobionic acid (4-O-β-D-galactopyranosyl-D-gluconic acid) is coupled to poly[α-(ω-aminoalkyl)glycolic acid]. The galactosyl unit of lactose provides a convenient targeting molecule toward hepatocyte cells because of the high affinity and avidity of the galactose receptor on these cells.

Other types of ligands that can be used include transferrin, epidermal growth factor (EGF), insulin, asialoorosomucoid, mannose-6-phosphate (monocytes), mannose (macrophage, some B cells), Lewis$^x$ and sialyl Lewis$^x$ (endothelial cells), N-acetyllactosamine (T cells), galactose (colon carcinoma cells), and thrombomodulin (mouse lung endothelial cells), fusogenic agents such as polymixin B and hemaglutinin HA2, lysosomotrophic agents, nucleus localization signals (NLS) such as T-antigen, and the like.

An advantage of the present invention is providing a gene carrier wherein the particle size and charge density are easily controlled. The particle size control is crucial for optimization of a gene delivery system because the particle size often governs the transfection efficiency, cytotoxicity, and tissue targeting in vivo. F. C. Szoka, 4 Bioconjugate Chem. 372–379 (1993). Generally, the size of a gene delivery particle should not exceed the size of a virus to enable its effective penetration in tissue. In the present invention, the particle size can be varied by using different molecular weights of polymers, which in turn determines the particle size of the polymer-nucleic acid complex.

In a preferred embodiment of the invention, the particle sizes will range from about 10 to 100 nm depending on the polymer composition and the mixing ratio of the components. It is known that particles, nanospheres, and microspheres of different sizes accumulate in different organs of the body after intravenous injection depending on the size of the particles injected. For example, particles of less than 50 nm diameter can pass through the fenestrations of the liver endothelium and become localized, perhaps after lymphatic transport, in the spleen, bone marrow, and possibly tumor tissue. Intravenous, intra-arterial, or intraperitoneal injection of particles approximately 0.1 to 2.0 μm diameter leads to rapid clearance of particles from the blood stream by macrophages of the reticuloendothelial system. The copolymers of the present invention can be used to manufacture dispersions of controlled particle size, which can be organ-targeted in the manner described herein.

It is believed that the presently claimed composition is effective in delivering a selected nucleic acid into hepatocytes by endocytosis mediated by galactosyl receptors on the surface of cells. The nucleic acid transfer to the other cells can be carried out by matching a cell having a selected receptor thereof with a selected sugar. For example, a carbohydrate-conjugated polyester can be prepared from a mannose-pendent copolymer for transfecting macrophage, an N-acetyllactosamine-pendent copolymer for transfecting T cells, and a glucose-pendent copolymer for transfecting colon carcinoma cells.

The polyester polymers of the present invention provide a highly positively charged polyester to generate biodegradable and amphiphilic copolymers, namely hydrophilic polycation and hydrophobic polyester block or graft copolymers, where the hydrophilic polycation block is large enough to endow water solubility to the copolymer, and to increase the cellular uptake of drug-loaded polymers. The hydrophilic cation is poly[α-(ω-aminoalkyl)glycolic acid], and carries a high positive charge to increase the cellular binding and uptake of polymers and drugs. The copolymer can be prepared as di-, tri-, or multi-block or graft copolymer, and more preferably is a diblock or graft copolymer. The hydrophobic polyester is preferably poly(L-lactic acid), poly(D-lactic acid), poly(glycolic acid), poly(L-lactic-co-glycolic acid) (PLGA), poly(D-lactic-co-glycolic acid), poly(ε-acprolactone), polybutyrolactone, and polypropiolactone, and more preferably is poly(L-lactic acid-co-glycolic acid). These amphiphilic copolymers are dispersible in water and can therefore be used to manufacture continuous release formulations of drugs without the use of high temperature or extremes of pH, and, for water-soluble drugs such as polypeptides and oligonucleotides, without exposure of the drug to organic solvents during manufacture. Such copolymers can be self-dispersible as synthesized, or copolymers that are not inherently self-dispersible can be rendered so by the processes described herein. The biodegradable amphiphilic copolymers of the present invention are also useful for the manufacture of sustained, continuous release injectable formulations of drugs. The copolymers of the present invention act as very efficient dispersing agents and can be administered by injection to give continuous delivery of lipophilic drugs. In addition, the biodegradable amphiphilic copolymer of the invention can be used to manufacture drug formulations that are targetable to particular organs of the human or animal body.

The present invention provides a biodegradable, non-toxic, non-viral vector for transferring; a selected nucleic acid into cells. The present invention provides an easy and efficient way to construct a diverse and well-defined structure and to functionalize the surface with diverse sugar ligands and fusogenic agents. In addition, the present invention provides a positively charged polyester block to increase the cellular binding and uptake of polymers.

The polymer of the present invention is directed to overcoming the problems presented by known polymers, as set forth above. For example, a biodegradable polyester of the present invention, poly[α-(ω-aminoalkyl)glycolic acid], is directly hydrolyzed into 6-amino-2-hydroxy hexanoic acid or 5-amino-2-hydroxy pentanoic acid, which are easily converted to lysine and ornithine in the body. Thus, the degradation products of the present polyester polymers are metabolites of naturally occurring amino acids. Poly[α-(ω-aminoalkyl)glycolic acid] is biodegradable in the body within a few weeks. The degradation products are small non-toxic molecules that are subject to renal excretion and are inert during the period required for gene expression.

Degradation is a simple hydrolytic and/or enzymatic reaction. Enzymatic degradation may be significant in certain organelles, such as lysosomes. The time needed for degradation can vary from days to months depending on the molecular weight and modifications of the polymers. Therefore, this polyester polymer overcomes the limitation of known polycationic polymers as gene carriers.

Figure 4:
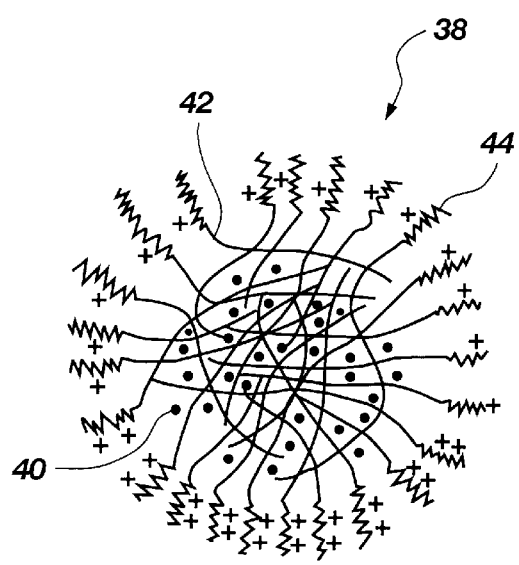
FIG. 4 shows a schematic representation of a nanoparticle or microsphere prepared from an amphiphilic block copolymer and drug according to the present invention.

Further, nanoparticles or microspheres can be conjugated with the amino-polyester polymer of the present invention. FIG. 4 shows an illustrative nanoparticle 38 loaded with a drug 40. The matrix of the nanoparticle is composed of a copolymer of PLGA 42 and poly[α-(ω-aminoalkyl)glycolic acid] 44. The nanoparticle has a hydrophobic interior due to the PLGA, but the surface is positively charged due to the cationic nature of the poly[α-(ω-aminoalkyl)glycolic acid]. The positively-charged polyester polymer can adhere to negatively-charged cell membrane, while the hydrophobic PLGA is loaded with drug.

The following examples illustrate the present invention and not intended to be limiting.

EXAMPLE 1

This example illustrates the preparation of poly[α-(4-aminobutyl)glycolic acid].

Alpha-(N-benzloxycarbonyl-4-aminobutyl) glycolic acid. A solution of $NaNO_2$ in water (200 ml) was added dropwise during 3 hr to an ice-cooled and stirred solution of N-ε-CBZ-L-lysine in 1 N $H_2SO_4$ and acetonitrile. The mixture was stirred for an additional 2 hr after the addition of 0–5° C. and left to stand overnight. The resulting clear solution was concentrated under reduced pressure. The residual semi-solid was extracted with ether, and the ether extract was then crystallized in ether/petroleum ether. The products were α-(N-CBZ4-aminobutyl) glycolic acid.

Poly[α-(N-benzyloxycarbonyl-4-aminobutyl) glycolic acid].

Three g of α-(N-CBZ-aminobutyl) glycolic acid was placed in a single-neck round bottom flask containing a stir bar and equipped with a vacuum distillation apparatus. The reaction flask was flushed thoroughly with nitrogen and the mixture was heated at 150° C. at reduced pressure (5 mmHg). The reaction time was varied from 3 days to 1 week to obtain diverse molecular weights of poly(N-CBZ-α-(aminobutyl)glycolic acid]. The product was obtained by precipitation with chloroform solution containing a large excess of methanol and characterized by GPC using polystyrene standards.

Deprotection of Poly[α-(N-benzyloxycarbonyl-4-aminobutyl) glycolic acid].

To a solution of poly[α-(N-CBZ-4-aminobutyl)glycolic acid] (300 mg) in DMF (4 ml) was added paladium catalyst (1 g). With vigorous stirring, 98% formic acid (14 ml) was slowly added to the mixture. The evolution of hydrogen was vigorous at first and ceased after about 1 hour. Stirring was continued at room temperature for 14 hours, and then the paladium catalyst was removed by filtration and washed with 20 ml of 1 N HCl. The washings were combined with the filtrate. The combined solution was concentrated to a total volume of 5 ml by partial evaporation under reduced pressure. The concentrated solution was then mixed with 1 N HCl (10 ml) to ensure the complete replacement of the formate salt by hydrochloric acid. Finally, the acidic polymer solution was added dropwise into a large excess of acetone, resulting in the precipitation of poly[α-(4-aminobutyl)glycolic acid] as a white powder.

EXAMPLE 2

In this example, poly[α-(3-aminopropyl)glycolic acid] was prepared according to the procedure of Example 1 except that N-δ-benzyloxycarbonyl-L-ornithine was substituted for N-ε-benzyloxycarbonyl-L-lysine.

EXAMPLE 3

In this example, poly[α-(5-aminopentyl)glycolic acid] was prepared according to the procedure of Example 1 except that α-(N-benzyloxycarbonyl-5-aminopentyl)-L-glycine was substituted for N-ε-benzyloxycarbonyl-L-lysine.

EXAMPLE 4

In this example, poly[α-(6-aminohexyl)glycolic acid] was prepared according to the procedure of Example 1 except that α-(N-benzyloxycarbonyl-6-aminohexyl)-L-glycine was substituted for N-ε-benzyloxycarbonyl-L-lysine.

EXAMPLE 5

In this example, poly[α-(7-aminoheptyl)glycolic acid] was prepared according to the procedure of Example 1 except that α-(N-benzyloxycarbonyl-7-aminoheptyl)-L-glycine was substituted for N-ε-benzyloxycarbonyl-L-lysine.

EXAMPLE 6

A solution of lactobionic acid (1.33 g) in dry tetrahydrofuran (50 ml) was neutralized with an equimolar amount of triethylamine (0.5 ml) followed by adding isobutyl chlorocarbonate (0.5 ml) at room temperature. After 10 minutes of stirring, the reaction mixture was added into a solution of poly[α-(4-aminobutyl)glycolic acid] (0.67 g) in dimethylsulfoxide (50 ml) and was then stirred for 20 minutes at room temperature. The reaction product of poly[α-(N-lactosyl-4-aminobutyl)glycolic acid] was obtained by filtration and precipitation in diethyl ether.

EXAMPLE 7

One g of poly(L-lactic acid) (MW 5,000) was dissolved in tetrahydrofuran, and then a twice molar amount of diaminoethane was added in the presence of dicyclohexylcarbodiimide to yield amine-terminated poly(L-lactic acid). After 2 hours of stirring at room temperature, the reaction product was obtained by precipitation in methanol. Amine-terminated poly(L-lactic acid) was reacted with an equimolar amount of poly[α-(N-benzyloxycarbonyl-4-aminobutyl) glycolic acid] (MW 2900), which was conducted in dimethylformamide at room temperature using dicyclohexylcarbodiimide, followed by the removal of benzyloxycarbonyl group by catalytic hydrogenation. The product of this reaction was poly[α-(4-aminobutyl)glycolic acid]-poly(L-lactic acid) diblock copolymer.

EXAMPLE 8

In this example, the procedure of Example 7 is followed except that poly[α-(4-aminobutyl)lactic acid] is substituted for poly(L-lactic acid). The product of the reaction is poly [α-(4-aminobutyl) glycolic acid]-poly[α-(4-aminobutyl) lactic acid] diblock copolymer.

EXAMPLE 9

One g of N-CBZ-α-(4-aminobutyl) glycolic acid and 10 g of L-lactic acid were placed in a single-neck round bottom flask containing a stir bar and equipped with a vacuum distillation apparatus. The reaction flask was flushed thoroughly with nitrogen, and the mixture was heated at 150° C.

under reduced pressure (5 mmHg). The reaction time was varied from 3 days to 1 week to obtain diverse molecular weights of poly[N-CBZ-α-(4-aminobutyl)glycolic acid]. The product was obtained by precipitation of chloroform solution in large excess amount of methanol, characterized by GPC using polystyrene standards, and followed by the removal of benzyloxycarbonyl group by catalytic hydrogenation. The product was poly[α-(4-aminobutyl)glycolic acid-co-L-lactic acid] random copolymer.

EXAMPLE 10

In this example there is illustrated the transfection and cytotoxicity testing of poly[α-(N-lactosyl-4-aminobutyl)glycolic acid]:DNA complex in human liver carcinoma cells (HepG2; ATCC accession no.: HB-8065).

In vitro transfection efficiency of the polyester polymer was tested on HepG2 cells grown in MEM medium with 10% fetal bovine serum. Cells were harvested and counted using a hemacytometer and plated in 96-well plates at a density of $2 \times 10^5$ cells/ml. One day later, various formulations of complexes comprising poly[α-(N-lactosyl4-aminobutyl)glycolic acid], prepared according to the procedure of Example 6, and pSV-β-gal plasmid DNA (Promega Corp., Madison, Wis.; EMBL accession No. X65335) were freshly prepared 30 minutes before transfection. The growth medium in each well of the 96-well plates was replaced by fresh growth medium without serum and the complexes were added to a final volume of 10 μl. After a 4 hour-incubation, the growth medium was replaced with a serum-containing medium and cells were further incubated for an additional 44 hours at 37° C. in a 5% $CO_2$ incubator. Cells were then harvested using 0.25% trypsin-EDTA treatment and cell lysates were obtained by adding 100 μl of 1×lysis buffer (Promega, Madison, Wis., cat. no. E3971) to each well.

Plasmid pSV-μ-gal is a positive control vector for monitoring transfection efficiencies of mammalian cells. The pSV-μ-gal plasmid contains a SV40 early promoter and enhancer sequence, transcription start sites, E. coli lacZ coding region encoding β-galactosidase, and SV40 small T antigen polyadenylation signals. SV40 early promoter and enhancer drive the transcription of the lacZ gene.

Transfection efficiency was measured by determining the β-galactosidase enzyme activity in cell lysates. Mixtures of equal amounts of cell lysates and O-nitrophenyl-β-D-galactopyranoside (ONPG, 1.33 mg/ml) in a 2×assay buffer (Promega; 200 mM sodium phosphate buffer, pH 7.3, 2 mM MgCl2, 100 mM 2-mercaptoethanol, 1.33 mg/ml ONPG) were incubated at 37° C. for 4 hours. The reaction was terminated by adding 150 μl of 1 M sodium carbonate solution to each well, and the absorbance at 420 nm was read with a spectrophotometer for the β-galactosidase activity. LIPOFECTIN reagent (GIBCO/BRL, Gaithersburg, Md.) was used as a control to compare the transfection efficiency. LIPOFECTIN reagent is a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water.

Cytotoxicity of the mixed polymeric micelles to HepG2 cells was determined by the MTT calorimetric assay originally described by T. Mosmann, Rapid Colorimetric Assay for Cellular Growth and Survival: Application to Proliferation and Cytotoxicity Assays, 65 J. Immunol. Methods 55–63 (1983), hereby incorporated by reference. Briefly, cells were harvested from exponentially growing culture and plated in 96-well plates at $2 \times 10^5$ cells/ml density. After a 24 hour-incubation period, cells were treated with varying amounts of poly[α-N-lactosyl-4-aminobutyl)glycolic acid] solution in the absence of serum. After a 4 hour-incubation, the growth medium was replaced with serum-containing growth medium and cells were further incubated for an additional 44 hours at 37° C. in a 5% $CO_2$ incubator. Then, 25 μl of 3-[4,5-dimethylthiozol-2-yl]-2,5-diphenyltetrazolium bromide (MTT) solution (final concentration, 0.5 mg/ml) was added to each well, followed by 4 hours of incubation at 37° C. Growth medium was carefully removed and 150 μl of DMSO was added to dissolve the formed formazan crystal. The optical density (OD) was measured at 570 nm using a Bio-Tek EL-3311 microplate reader (Bio-Tek Instrument, Winooski, Vt.). Cell viability (%) was calculated according to the following equation:

$$\text{Viability (\%)} = [OD_{570} \text{ (sample)}/OD_{570} \text{ (control)}] \times 100$$

where the $OD_{570}$ (control) represents the measurement from the wells treated with PBS buffer only and the $OD_{570}$ (sample) represents the measurement from the wells treated with varying amounts of polymer.

We claim:

1. A biodegradable polyester polymer represented by the formula

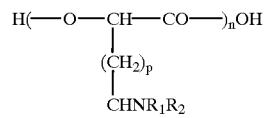

wherein n is a positive integer representing the number of repeating monomer units; p is an integer from 2 to 9; and $R_1$ and $R_2$ are selected from the group consisting of H, carbohydrates and derivatives thereof, polyethylene glycol, biologically active compounds, and peptides.

2. The polymer of claim 1 wherein $R_1$ or $R_2$ is selected from the group consisting of galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, lactobionic acid, folate, hyalunic acid, polyethylene glycol, transferrin, epidermal growth factor, insulin, asialoorosomucoid, mannose-6-phosphate, Lewis$^x$ and sialyl Lewis$^x$, fusogenic agents, lysosomotrophic agents, and nucleus localizing signal.

3. The polymer of claim 2 wherein said fusogenic agent is a member selected from the group consisting of polymixin B and hemaglutinin HA2.

4. The polymer of claim 2 wherein said nucleus localizing signal is T-antigen.

5. The polymer of claim 1 wherein $R_1$ or $R_2$ is polyethylene glycol.

6. The polymer of claim 5 further comprising a functional moiety bonded to the polyethylene glycol, wherein said functional moiety is a member selected from the group consisting of biologically active compounds, galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, lactobionic acid, folate, hyalunic acid, transferrin, epidermal growth factor, insulin, asialoorosomucoid, mannose-6-phosphate, Lewis$^x$ and sialyl Lewis$^x$, fusogenic agents, lysosomotrophic agents, and nucleus localizing signal.

7. A biodegradable, amphiphilic polyester block copolymer comprising:

(a) a first polymer represented by the formula $$H(\!\!-\!\!O\!\!-\!\!\underset{\underset{\underset{CHNR_1R_2}{|}}{(CH_2)_p}}{\overset{|}{CH}}\!\!-\!\!CO\!\!-\!\!)_n OH$$

wherein n is a positive integer representing the number of repeating monomer units; p is an integer from 2 to 9; and $R_1$ and $R_2$ are selected from the group consisting of H, carbohydrates and derivatives thereof, polyethylene glycol, biologically active compounds, and peptides; and (b) a second polymer bonded to the first polymer, wherein the second polymer is a member selected from the group consisting of poly(D-lactic acid), poly(L-lactic acid), poly(DL-lactic acid), poly(D-lactide), poly(L-lactide), poly(DL-lactide), polyglycolic acid, polyglycolides, poly(lactic-co-glycolic acids), and polycaprolactone.

8. The copolymer of claim 7 wherein $R_1$ or $R_2$ is a member selected from the group consisting of galactose, glucose, fucose, fructose, lactose; sucrose, mannose, cellobiose, nytrose, triose, dextrose, trehalose, maltose, galactosamine, glucosamine, galacturonic acid, glucuronic acid, gluconic acid, lactobionic acid, folate, hyalunic acid, polyethylene glycol, transferrin, epidermal growth factor, insulin, asialoorosomucoid, mannose-6-phosphate, Lewis$^x$ and sialyl Lewis$^x$, fusogenic agents, lysosomotrophic agents, and nucleus localizing signal.

9. A biodegradable polyester random copolymer comprising:

(a) a plurality of a first monomer represented by the formula $$HO\!\!-\!\!\underset{\underset{\underset{CHNR_1R_2}{|}}{(CH_2)_p}}{\overset{|}{CH}}\!\!-\!\!COOH$$

wherein p is an integer from 2 to 9; and $R_1$ and $R_2$ are selected from the group consisting of H, carbohydrates and derivatives thereof, polyethylene glycol, biologically active compounds, and peptides; and (b) a plurality of a second monomer selected from the group consisting of D-lactic acid, L-lactic acid, D-lactide, L-lactide, glycolic acid, glycolide, and caprolactone.

10. The copolymer of claim 9 wherein $R_1$ or $R_2$ is a member selected from the group consisting of galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, lactobionic acid, folate, hyalunic acid, polyethylene glycol, transferrin, epidermal growth factor, insulin, asialoorosomucoid, mannose-6-phosphate, Lewis$^x$ and sialyl Lewis$^x$, fusogenic agents, lysosomotrophic agents, and nucleus localizing signal.

11. A composition comprising a bioactive agent electrostatically coupled to a biodegradable polyester polymer represented by the formula $$H(\!\!-\!\!O\!\!-\!\!\underset{\underset{\underset{CHNR_1R_2}{|}}{(CH_2)_p}}{\overset{|}{CH}}\!\!-\!\!CO\!\!-\!\!)_n OH$$

wherein n is a positive integer representing the number of repeating monomer units; p is an integer from 2 to 9; and $R_1$ and $R_2$ are selected from the group consisting of H, carbohydrates and derivatives thereof, polyethylene glycol, biologically active compounds, and peptides.

12. The composition of claim 11 wherein $R_1$ or $R_2$ is a member selected from the group consisting of galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, lactobionic acid, folate, hyalunic acid, polyethylene glycol, transferrin, epidermal growth factor, insulin, asialoorosomucoid, mannose-6-phosphate, Lewis$^x$ and sialyl Lewis$^x$, fusogenic agents, lysosomotrophic agents, and nucleus localizing signal.

13. The composition of claim 12 wherein said bioactive agent is a nucleic acid.

14. The composition of claim 13 wherein said nucleic acid is DNA.

15. A composition comprising a bioactive agent electrostatically coupled to a biodegradable, amphiphilic polyester block copolymer comprising:

(a) a first polymer represented by the formula $$H(\!\!-\!\!O\!\!-\!\!\underset{\underset{\underset{CHNR_1R_2}{|}}{(CH_2)_p}}{\overset{|}{CH}}\!\!-\!\!CO\!\!-\!\!)_n OH$$

wherein n is a positive integer representing the number of repeating monomer units; p is an integer from 2 to 9; and $R_1$ and $R_2$ are selected from the group consisting of H, carbohydrates and derivatives thereof, polyethylene glycol, biologically active compounds, and peptides; and (b) a second polymer bonded to the first polymer, wherein the second polymer is a member selected from the group consisting of poly(D-lactic acid), poly(L-lactic acid), poly(DL-lactic acid), poly(D-lactide), poly(L-lactide), poly(DL-lactide), polyglycolic acid, polyglycolides, poly(lactic-co-glycolic acids), and polycaprolactone.

16. The composition of claim 15 wherein $R_1$ or $R_2$ is a member selected from the group consisting of galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, lactobionic acid, folate, hyalunic acid, polyethylene glycol, transferrin, epidermal growth factor, insulin, asialoorosomucoid, mannose-6-phosphate, Lewis$^x$ and sialyl Lewis$^x$, fusogenic agents, lysosomotrophic agents, and nucleus localizing signal.

17. The composition of claim 15 wherein said bioactive agent is a nucleic acid.

18. The composition of claim 17 wherein said nucleic acid is DNA.

19. A composition comprising a bioactive agent electrostatically coupled to a biodegradable polyester random copolymer comprising:

(a) a plurality of a first monomer represented by the formula

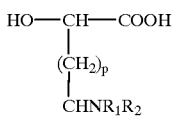

wherein p is an integer from 2 to 9; and $R_1$ and $R_2$ are selected from the group consisting of H, carbohydrates and derivatives thereof, polyethylene glycol, and peptides; and (b) a plurality of a second monomer selected from the group consisting of D-lactic acid, L-lactic acid, D-lactide, L-lactide, glycolic acid, glycolide, and caprolactone.

20. The composition of claim 19 wherein $R_1$ or $R_2$ is a member selected from the group consisting of galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, lactobionic acid, folate, hyalunic acid, polyethylene glycol, transferrin, epidermal growth factor, insulin, asialoorosomucoid, mannose-6-phosphate, Lewis$^x$ and sialyl Lewis$^x$, fusogenic agents, lysosomotrophic agents, and nucleus localizing signal.

21. The composition of claim 19 wherein said bioactive agent is a nucleic acid.

22. The composition of claim 21 wherein said nucleic acid is DNA.

23. A composition comprising a mixture of a biologically active compound and a member selected from the group consisting of:

(a) a biodegradable polyester polymer represented by the formula

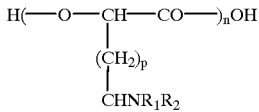

wherein n is a positive integer representing the number of repeating monomer units; p is an integer from 2 to 9; and $R_1$ and $R_2$ are selected from the group consisting of H, carboydrates and derivatives thereof, polyethylene glycol, biologically active compounds, and peptides;

(b) a biodegradable, amphiphilic polyester block copolymer comprising:

(i) a first polymer represented by the formula

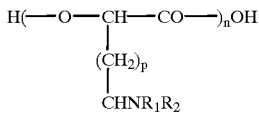

wherein n is a positive integer representing the number of repeating monomer units; p is an integer from 2 to 9; and $R_1$ and $R_2$ are selected from the group consisting of H, carbohydrates and derivatives thereof, polyethylene glycol, biologically active compounds, and peptides; and (ii) a second polymer bonded to the first polymer, wherein the second polymer is a member selected from the group consisting of poly(D-lactic acid), poly(L-lactic acid), poly(DL-lactic acid), poly(D-lactide), poly(L-lactide), poly(DL-lactide), polyglycolic acid, polyglycolides, poly(lactic-coglycolic acids), and polycaprolactone; and (c) a biodegradable polyester random copolymer comprising:

(i) a plurality of a first monomer represented by the formula

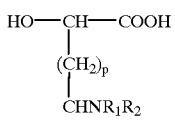

wherein p is an integer from 2 to 9; and $R_1$ and $R_2$ are selected from the group consisting of H, carbohydrates and derivatives thereof, polyethylene glycol, biologically active compounds, and peptides; and (ii) a plurality of a second monomer selected from the group consisting of D-lactic acid, L-lactic acid, D-lactide, L-lactide, glycolic acid, glycolide, and caprolactone.

* * * * *